(12) United States Patent
Matthews

(10) Patent No.: US 6,365,181 B1
(45) Date of Patent: Apr. 2, 2002

(54) THIXATROPIC GELATIN CARRIER COMPOSITION

(75) Inventor: James W. Matthews, Newport, RI (US)

(73) Assignee: Gattefosse Corporation, Westwood, NJ (US)

( * ) Notice: Subject to any disclaimer, the term of this patent is extended or adjusted under 35 U.S.C. 154(b) by 0 days.

(21) Appl. No.: 09/553,588

(22) Filed: Apr. 20, 2000

(51) Int. Cl.⁷ .................................................. A61K 9/48
(52) U.S. Cl. ........................ 424/451; 424/452; 424/456; 514/962
(58) Field of Search ................................ 424/456, 408, 424/455, 451, 452; 514/962

(56) References Cited

U.S. PATENT DOCUMENTS

| | | | |
|---|---|---|---|
| 4,020,159 A | * | 4/1977 | Hermann .................... 424/180 |
| 4,126,672 A | * | 11/1978 | Sheth et al. ................. 424/22 |
| 4,612,187 A | | 9/1986 | Iijima et al. |
| 4,662,155 A | * | 5/1987 | Chasman ..................... 53/433 |
| 4,701,327 A | | 10/1987 | Henmi et al. |
| 4,708,834 A | | 11/1987 | Cohen et al. |
| 4,935,243 A | | 6/1990 | Borkan et al. |
| 5,140,021 A | | 8/1992 | Maxson et al. |
| 5,173,496 A | | 12/1992 | Bruneau et al. |
| 5,175,002 A | | 12/1992 | Torosian |
| 5,271,946 A | | 12/1993 | Hettche |
| 5,275,821 A | | 1/1994 | Torosian |
| 5,443,836 A | | 8/1995 | Downey et al. |
| 5,496,556 A | | 3/1996 | Johnson et al. |
| 5,538,737 A | | 7/1996 | Leonard et al. |
| 5,582,839 A | | 12/1996 | McCarty et al. |
| 5,595,758 A | | 1/1997 | Adusumilli et al. |
| 5,597,582 A | | 1/1997 | Brown et al. |
| 5,609,909 A | | 3/1997 | Meyer et al. |
| 5,637,310 A | | 6/1997 | Johnson |
| 5,645,856 A | | 7/1997 | Lacy et al. |
| 5,651,983 A | | 7/1997 | Kelm et al. |
| 5,686,105 A | | 11/1997 | Kelm et al. |
| 5,686,106 A | | 11/1997 | Kelm et al. |
| 5,738,871 A | | 4/1998 | Story et al. |
| 5,776,498 A | | 7/1998 | McCarty |
| 5,776,504 A | | 7/1998 | McCarty |
| 5,814,338 A | | 9/1998 | Veronesi |
| 5,817,323 A | | 10/1998 | Hutchinson et al. |
| 5,876,757 A | | 3/1999 | McCarty |
| 5,916,591 A | | 6/1999 | Bierdel-Willkommen et al. |
| 5,919,482 A | | 7/1999 | Marttila et al. |
| 5,961,970 A | | 10/1999 | Lowell et al. |
| 6,013,279 A | | 1/2000 | Klett-Loch et al. |
| 6,193,991 B1 | * | 2/2001 | Shukla ........................ 424/426 |

* cited by examiner

*Primary Examiner*—Jose' G. Dees
*Assistant Examiner*—Sharmila S. Gollamudi
(74) *Attorney, Agent, or Firm*—Norris, McLaughlin & Marcus

(57) ABSTRACT

A thixatropic gelatin carrier composition which is used as a vehicle in the manufacture of soft or hard gelatin capsule. The composition comprises from about 84% to 95% of a vegetable oil, from about 1% to 9% of a viscosity modifier and from about 1% to 15% of a surface active agent. When the carrier composition is stirred it becomes fluid and active solids are dispersed in the carrier during stirring. When the stirring is stopped, the carrier becomes a semi-solid and maintains the active solids in a stable uniform dispersion. Up to about 50% by weight of active solids can be dispersed in the carrier composition and the active solids can include vitamins, pharmaceuticals or nutriceuticals or combinations thereof.

14 Claims, No Drawings

THIXATROPIC GELATIN CARRIER COMPOSITION

BACKGROUND OF THE INVENTION

1. Field of the Invention

The invention has to do with carrier compositions which are used as vehicles in the manufacture of soft or hard gelatin capsules. More specifically, the invention relates to a gelatin carrier composition having thixatropic properties and substantial capacity to suspend active materials in a uniform dispersion.

2. The Related Art

Gelatin capsule products which are used for oral or suppository delivery of active agents are prepared by filling a hard or soft gelatin capsule with a carrier composition having the active agent incorporated therein. Prior art carrier compositions are either liquid at ambient temperature or they become liquid with heating and they are poured into the hard or soft capsules as a liquid. When the carrier compositions are liquid at ambient temperature, the active agents incorporated therein must be dissolved, they cannot be added at high loadings and it is difficult to maintain them in a uniform distribution within the capsule. Carrier compositions that are solid at ambient temperature require heating before they can be poured into the capsules and the heat can damage the capsule walls, reduce the activity of the active ingredient or damage other heat sensitive ingredients.

Oil based drug delivery systems for hydrophobic drugs are described in U.S. Pat. No. 5,645,856. The systems comprise a digestible oil and surfactant for dispensing the oil in vivo upon administration of the carrier system. The surfactant has hydrophilic and lipophilic components and the general composition of the system can be from 10–90% digestible oil, 10–60% hydrophilic surfactant and 5–60% lipophilic surfactant.

In U.S. Pat. No. 5,738,871, a hard gelatin capsule system is described for the delivery of fat soluble nutrients such as a fat-soluble vitamin (A, D, E or K) or an unsaturated fatty acid glyceride. Natural oils which are a mixture of fat soluble nutrients may be used in combination with a non-ionic surfactant, a gelatin softening agent and, optionally, water. The surfactant is present in an amount from 30% to 99% based on the total weight of the formulation used for filling the capsules.

Soft gelatin capsules are described in U.S. Pat. No. 4,701,327 as made by forming capsule shells with an ordinary grade gelatin dissolved in water and adjusted to pH 3.7 to 5.7 by the addition of pharmacologically acceptable acids.

The improvement of the present invention is the discovery of a vegetable oil based carrier composition which has thixatropic properties. Active agents are easily admixed with the carrier composition by stirring and high loadings of the active agents can be used to make a stable uniform dispersion within the carrier composition because the composition becomes semi-solid when stirring is stopped.

Advantages of the present invention include use of reduced labor to manufacture the carrier composition. The composition of the invention prevents separation of solid ingredients from the carrier prior to and after encapsulation and improves the stability of heat sensitive materials by eliminating or reducing the application of heat during processing. Lecithin and similar materials which retard the sealing of gelatin surfaces are not ingredients of the carrier composition of the invention and sealing problems are accordingly avoided.

The carrier composition of the present invention also permits digestive fluids to separate the active agents more rapidly from the carrier, thereby increasing the absorption of the active agents.

All of the ingredients used to make the carrier composition of the invention are food grade or pharmaceutically acceptable.

All percentages set forth herein are by weight/weight and all parts are by weight.

SUMMARY OF THE INVENTION

The carrier composition of the invention is a thixatropic carrier gel comprising a homogeneous dispersion of viscosity modifiers and surface active agents in vegetable oil. When the carrier composition is agitated, such as by slow stirring, it becomes fluid and when the agitation is stopped, it becomes a highly viscous semi-solid. Active agents are dispersed in the carrier composition during stirring and the material is then encapsulated. Because the carrier composition becomes a semi-solid when agitation ceases, the active solids are maintained in a stable uniform dispersion within the carrier.

The components of the carrier composition include from about 84% to 95% of a vegetable oil, from about 1% to 9% of a viscosity modifier and from about 1% to 15% of a surface active agent such that the total amounts to 100%.

Active agents which can be suspended in the carrier composition of the invention are generally in the form of fine powders and they include vitamins, pharmaceuticals, nutriceuticals and the like. These active agents are admixed with the carrier composition at loadings of up to about 50% incorporated solids based on the total weight of the carrier composition and the admixture is then filled into either hard or soft gelatin capsules.

The carrier composition is manufactured by admixing the ingredients. In the preferred embodiment, a dispersion of the carrier composition is manufactured by heating the vegetable oil to a temperature of from about 25° to 35° C., adding the surface active agent with agitation until uniformly distributed, heating the viscosity modifier to its melting point temperature plus up to about 5° C. and then adding it slowly to the vegetable oil/surface active agent mixture with agitation, homogenizing the product and cooling to ambient temperature of about 23° to 28° C. A deaeration step may be employed following homogenization and before cooling to improve uniformity of the carrier composition product. The product then is ready for use as a carrier composition.

DESCRIPTION OF THE PREFERRED EMBODIMENTS

Suitable vegetable oils for use according to the invention include soybean oil, rapeseed oil, palm oil and cottonseed oil. The oils can be used individually or in blends and a preferred oil composition is soybean oil.

The viscosity modifier is food grade or pharmaceutically acceptable and preferably is selected from the group consisting of glyceryl palmito stearate and glyceryl behenate and equivalent compositions as will be apparent to those skilled in the art. Commercially available viscosity modifiers which are suitable for use according to the invention are COMPRITOL 888 ATO and PRECIROL ATO-5 available from Gattefossé Corp., 372 Kinderkamack Road, Westwood, N.J. 07675 USA.

The surface active agent is food grade or pharmaceutically acceptable and preferably is polyglyceryloleate and equivalent compositions as will be apparent to those skilled in the art. A commercially available surface active agent which is suitable for use according to the invention is PLUROL OLEIQUE C C 497 also available from Gattefossé.

The carrier composition of the invention is made by heating the vegetable oil to a temperature from about 25° C. to about 35° C. followed by admixing the surface active agent therein to make a vegetable oil/surface active agent mixture. The viscosity modifier is melted and heated to a sufficient temperature to assure complete phase change, preferably up to about 5° C. above its melting point, and then it is admixed with the vegetable oil/surface active agent mixture to make a product mixture. The product mixture is then homogenized using conventional equipment such as high shear rotational equipment or high pressure discharge equipment and then it is cooled to ambient temperature of about 23° to 28° C. to provide the carrier composition of the invention at ambient temperature. As an option, the product mixture can be deaerated following homogenizing but before cooling. Deaeration can be achieved by using vacuum in a vessel or a moving disc apparatus.

The carrier composition is an amber colored translucent semi-solid which becomes fluid when it is gently mixed. Active agents in powdered form can be admixed with the carrier composition at loadings of up to about 50% of active agent by total weight of the carrier composition/active agent mixture. There is no need to heat the carrier composition in order to incorporate the active agent. Stirring the carrier composition without heating makes it sufficiently fluid to incorporate the active agent and this is the preferred method of the invention. As an option, however, the carrier composition can be heated from about 25° C. to about 35° C. prior to admixing an active agent therein. The carrier composition/active agent mixture is filled into a hard or soft gelatin capsule for oral ingestion or use as a suppository. As an option, the mixture can be slightly heated to from about 25° C. to about 35° C. before it is filled into capsules.

EXAMPLES

The following examples are provided to illustrate embodiments of the invention without limiting the scope thereof.

Example 1

In a jacketed kettle, 3.000 kilograms of PRECIROL ATO-5 glyceryl palmitostearate was heated at 60° C. until it was fully melted. Ninety-two (92.000) kilograms of a blend of soybean and rape seed oil was admixed, in a vessel fitted with a mixer, with 5.000 kilograms of PLUROL OLEIQUE C C 497 polyglyceryl oleate until thoroughly incorporated. Mixing was then continued while the melted glyceryl palmitostearate was added at a constant rate until it was fully dispersed. The resulting mixture was then passed through a high shear rotational homogenizer to produce a uniform liquid which then was deaerated in a rotating disc deaerator. The product was poured into containers, hermetically sealed therein and allowed to cool to ambient temperature.

Example 2

The product of Example 1 was used to make a Vitamin B complex for filling into capsules.

1.15 kilograms ("kg.") of powdered Riboflavin (Vitamin $B_2$) and 2.3 kg. of powdered Piridoxine HCl (Vitamin $B_6$) were passed through a #80 US Testing Screen. The product of Example 1 in an amount of 96.55 kg. was added to a vessel fitted with a mixer and mixed until it was completely liquefied. With continued mixing, the screened powder was slowly added until it was uniformly dispersed therein as a suspension. The completed suspension was deaerated in a vacuum vessel and then stored in a sealed container followed by filling into oblong shaped clear capsules.

Example 3

Accelerated stability testing was conducted on capsules made according to Example 2 and on capsules made with the same amounts of Vitamins $B_2$ and $B_6$ wherein an oil/beeswax base was used as the carrier instead of the composition of Example 1. The capsules were filled into 180 cc white high density polyethylene bottles and stored at 40° C. and 75% relative humidity. However, the testing illustrated that the stability of the vitamins was about the same using the carrier compositions of the invention and the prior art beeswax based compositions. But the dissolution of the vitamins in the carrier composition of the invention was substantially higher (generally about 10 times higher) than the dissolution in the prior art beeswax composition. The results are summarized in Tables 1 and 2 below. In the Tables, the term "NLT" means not less than, the term "RSD" means relative standard deviation and the term "Standard" means comparison with a standard capsule of that physical size and shape.

TABLE 1

Vitamin $B_2/B_6$ in Softgel Capsules with an Oil/Beeswax Base

| TEST | SPECIFICATION | METHOD | RESULT | 1st MONTH | 2nd MONTH | | 3rd MONTH | |
|---|---|---|---|---|---|---|---|---|
| Description | Oblong shaped clear capsule containing yellow, semi-oily liquid | Visual | Compares to Standard | Compares to Standard | Compares to Standard w/Fill Separation | | Compares to Standard w/Fill Separation | |
| Dissolution | NLT 75% of assayed amount of riboflavin after 60 minutes | USP | 0.38 mg. (7.9%) | 0.21 mg. (4.6%) | $B_2$ 0.30 mg (7.3%) $B_6$ 3.5 mg (39.3%) | RSD: 45.0% 27.8% | $B_2$ 0.44 mg (9.0%) $B_6$ 2.3 mg (24.0%) | RSD: 77.5% 32.3% |
| Assay | | | | | | | | |
| Vitamin $B_2$ | 5.0 mg (90%– | USP | 4.8 mg | 4.52 mg | 4.1 mg (82.0%) | | 4.9 mg (98.0%) | |

TABLE 1-continued

Vitamin $B_2/B_6$ in Softgel Capsules with an Oil/Beeswax Base

| TEST | SPECIFICATION | METHOD | RESULT | 1st MONTH | 2nd MONTH | 3rd MONTH |
|---|---|---|---|---|---|---|
| (Riboflavin) | 150.0%) | | (96.0%) | (90.4%) | | |
| Vitamin $B_6$ (Pyridoxine) | 10.0 mg (90.0%–150.0%) | USP | 9.5 mg (95.0%) | 9.3 mg (93.0%) | 8.9 mg (89.0%) | 9.6 mg (96.9%) |

TABLE 2

Vitamin $B_2/B_6$ in Softgel Capsules with Carrier Composition of Example 1

| TEST | SPECIFICATION | METHOD | RESULT | 1st MONTH | 2nd MONTH | 3rd MONTH |
|---|---|---|---|---|---|---|
| Description | Oblong shaped clear capsule containing yellow, semi-oily liquid | Visual | Compares to Standard | Compares to Standard | Compares to Standard w/Fill Separation | Compares to Standard w/Fill Separation |
| Dissolution | NLT 75% of assayed amount of riboflavin after 60 minutes | USP | 2.6 mg (61.9%) | 3.6 mg (75.9%) | $B_2$ 2.9 mg (65.9%) RSD: 13.0% $B_6$ 9.41 mg (99.0%) RSD: 1.9% | $B_2$ 3.0 mg (73.2%) RSD: 38.3% $B_6$ 9.0 mg (96.8%) RSD: 4.2% |
| Assay | | | | | | |
| Vitamin $B_2$ (Riboflavin) | 5.0 mg (90%–150.0%) | USP | 4.2 mg (84.0%) | 4.74 mg (94.8%) | 4.4 mg (88.0%) | 4.1 mg (82.0%) |
| Vitamin $B_6$ (Pyridoxine) | 10.0 mg (90.0%–150.0%) | USP | 9.4 mg (94.0%) | 9.6 mg (96.0%) | 9.5 mg (95.0%) | 9.3 mg (93.0%) |

What is claimed is:

1. A carrier composition for use as a vehicle in the manufacture of soft or hard gelatin capsules comprising from about 84% to about 95% vegetable oil, from about 1% to about 9% of a viscosity modifier selected from the group consisting of glyceryl palmito stearate and glyceryl behenate and from about 1% to about 15% of a surface active agent wherein the carrier composition is a semi-solid which becomes fluid when stirred.

2. The composition of claim 1 wherein the vegetable oil is selected from the group consisting of soybean oil, rapeseed oil, palm oil and cottonseed oil.

3. The composition of claim 2 wherein the surface active agent is polyglyceryloleate.

4. A method of making a carrier composition for use as a vehicle in the manufacture of soft or hard gelatin capsules comprising heating from about 84 to 95 parts by weight of vegetable oil to a temperature from about 25° C. to about 30° C., admixing from about 1 to about 15 parts by weight of a surface active agent to make a vegetable oil/surface active agent mixture, melting a viscosity modifier selected from the group consisting of glyceryl palmito stearate and glyceryl behenate and heating the melted viscosity modifier to a temperature up to about 5° C. above its melting point followed by admixing from about 1 to about 9 parts by weight of the viscosity modifier with the vegetable oil/surface active agent mixture such that the total parts by weight is 100 parts of a product mixture, homogenizing the product mixture and cooling to about 25° C. wherein the carrier composition is a semi-solid which becomes fluid when stirred.

5. The method of claim 4 comprising the further step of deaeration following homogenizing.

6. The method of claim 4 wherein the vegetable oil is selected from the group consisting of soybean oil, rapeseed oil, palm oil and cottonseed oil.

7. The method of claim 6 wherein the surface active agent is polyglyceryloleate.

8. A composition comprising a semi-solid carrier in which 100% of the carrier comprises from about 84% to about 95% vegetable oil, from about 1% to about 9% of a viscosity modifier selected from the group consisting of glyceryl palmito stearate and glyceryl behenate and from about 1% to about 15% of a surface active agent and active agent admixed with the carrier at loading of up to about 50% of active agent by total weight of the carrier composition/active agent admixture.

9. The composition of claim 8 wherein the active agent is selected from the group consisting of vitamins, pharmaceuticals and nutriceuticals.

10. A method of making a composition having a semi-solid carrier in which 100% of the carrier comprises from about 84% to about 95% vegetable oil, from about 1% to about 9% of a viscosity modifier selected from the group consisting of glyceryl palmito stearate and glyceryl behenate and from about 1% to about 15% of a surface active agent and an active agent comprising admixing without heating the active agent with the carrier at loadings of up to about 50% of active agent by total weight of the carrier composition/active agent admixture.

11. A hard or soft gelatin capsule having incorporated therein a composition of claim 8.

12. A method of making a hard or soft gelatin capsule comprising filling the hard or soft gelatin capsule with a composition having a semi-solid carrier in which 100% of the carrier comprises from about 84% to about 95% vegetable oil, from about 1% to about 9% of a viscosity modifier selected from the group consisting of glyceryl palmito stearate and glyceryl behenate and from about 1% to about 15% of a surface active agent and active agent admixed with the carrier at loadings of up to about 50% of active agent by total weight of the carrier composition/active agent admixture.

13. The method of claim 12 wherein the composition is heated to from about 25° C. to about 35° C. prior to filling the hard or soft gelatin capsule.

14. The method of claim 10 wherein the carrier and the active agent are admixed with heating at a temperature of about 25° C. to about 35° C.

* * * * *